United States Patent [19]
Wang et al.

[11] Patent Number: 5,490,909
[45] Date of Patent: Feb. 13, 1996

[54] USE OF CAPILLARY ELECTROPHORESIS FOR QUANTITATING THE CONCENTRATION OF PROTEIN COMPONENTS AND OF THE TOTAL PROTEIN IN FLUIDS

[75] Inventors: Hann-Ping Wang; Cheng-Ming Liu, both of Yorba Linda, Calif.

[73] Assignee: Beckman Instruments, Inc., Fullerton, Calif.

[21] Appl. No.: 489,252

[22] Filed: Jun. 14, 1995

Related U.S. Application Data

[63] Continuation of Ser. No. 133,514, Oct. 7, 1993, abandoned.
[51] Int. Cl.$^6$ .................................................. B01D 57/00
[52] U.S. Cl. .................................................. 204/452
[58] Field of Search ........................... 204/180.1, 182.8, 204/299 R

[56] References Cited

U.S. PATENT DOCUMENTS

| | | | |
|---|---|---|---|
| 4,575,808 | 3/1986 | Kaneko | 364/558 |
| 4,927,265 | 5/1990 | Brownlee | 356/73 |
| 5,120,413 | 6/1992 | Chen et al. | 204/180 |
| 5,139,630 | 8/1992 | Chen | 204/180.1 |
| 5,145,567 | 9/1992 | Hsieh et al. | 204/180.1 |
| 5,202,006 | 4/1993 | Chen | 204/180.1 |
| 5,310,462 | 5/1994 | Chen | 204/299 R |

OTHER PUBLICATIONS

Donald E. Oken, *Quantitation of Picogram Quantities of Serum Albumin by Ultramicrodisc Electrophoresis and Direct Densitometry*, Microchemical Journal, 15, pp. 557–653 (1970).

*Primary Examiner*—John Niebling
*Assistant Examiner*—C. Delacroix-Muirheid
*Attorney, Agent, or Firm*—William H. May; Gary T. Hampson; Merchant & Gould

[57] ABSTRACT

A method of quantitating proteins in complex samples using capillary electrophoresis can be used both to determine the concentration of a protein in a sample and to determine total protein concentration in the sample. In general, the method of determining the concentration of a marker protein comprises: (1) adding a known quantity of an internal standard compound to a sample containing at least one protein, the internal standard compound selected from the group consisting of benzoic acid substituted with at least one halogen, producing a detector signal in relation to its concentration, and being capable of electrophoretic separation from the protein; (2) subjecting the sample and the internal standard compound to capillary electrophoresis to separate the protein and the internal standard compound from each other and from other components in the sample; (3) measuring the detector signal produced by the internal standard compound and a detector signal produced by the protein to determine a ratio of protein signal to internal standard signal; and (4) determining the concentration of the protein in the sample from a standard curve of protein concentration versus the ratio of protein signal to internal standard signal. A typical protein measurable by the method is albumin. Typically, measurements are made at 214 nm and the internal standard compound is 2,4-dichlorobenzoic acid.

28 Claims, 7 Drawing Sheets

USE OF CAPILLARY ELECTROPHORESIS FOR QUANTITATING THE CONCENTRATION OF PROTEIN COMPONENTS AND OF THE TOTAL PROTEIN IN FLUIDS

This is a File Wrapper Continuation of application Ser. No. 08/133,514, filed Oct. 7, 1993 now abandoned.

BACKGROUND

This invention relates to a method for determining a protein component in a fluid and/or determining the total protein concentration in the fluid.

In many situations, it is important to know both the concentration of a single marker protein, such as serum albumin, and the total protein concentration in a biological fluid, such as serum, urine, or cerebrospinal fluid. For example, human serum albumin is frequently assayed in biological samples for any one of a number of reasons. The concentration of this protein can be used to detect protein catabolism as the result of tissue damage or inflammation, the reduced absorption of amino acids caused by malabsorption syndromes or malnutrition, protein loss due to kidney disorders such as nephrotic syndrome or chronic glomuleronephritis, or other conditions affecting protein metabolism and balance. One condition in which human serum albumin occurs at low concentrations in urine is diabetes mellitus.

Other proteins found in serum, such as $\alpha_1$-antitrypsin, $\alpha_1$-acid glycoprotein, and C-reactive protein, are all markers of inflammation, particularly in the acute phase. Still other proteins, such as $\alpha_1$-fetoprotein and carcinoembryonic antigen, are also frequently monitored as potential markers of malignant disorder. Other proteins are frequently assayed as markers for particular disease states or inflammatory conditions.

Typically, quantitative protein determination of serum is done by nephelometric methods or colorimetric methods. Qualitative analysis of serum is typically done by gel electrophoresis in one or two dimensions. In a few cases of extremely abundant proteins, such as human serum albumin, dye binding methods are available, such as the determination of albumin with bromocresol green.

However, those methods that give qualitative separation and determinations of the proteins in a complex biological sample such as plasma, such as two-dimensional electrophoresis, cannot readily give accurate quantitative determinations of either the concentration of a particular protein of interest or of the total protein concentration in the sample. Similarly, methods that determine total protein concentration accurately cannot determine the concentration of particular proteins in the sample. Thus, multiple tests must be done to obtain both of these results. This requires additional instrumentation, more samples, and more time. It also increases the likelihood of error or contamination occurring in one of the tests.

Thus, there is a need for an improved method of protein determination that yields a qualitative analysis of the proteins in a sample and also yields the concentration of any particular protein in the sample as well as the total protein concentration. Preferably, such a method is suitable for the determination of a large number of proteins and can operate over a wide range of protein concentrations. Preferably, the method can handle a wide range of biological samples as well as non-biological samples, including urine, cerebral spinal fluid, tears, seminal fluid or vaginal fluid, and environmental waste samples.

SUMMARY

We have invented a method of quantitating proteins in complex samples using capillary electrophoresis. The method can be used both to determine the concentration of a single protein in a sample and to determine total protein concentration in the sample.

In general, the method of determining the concentration of a single protein in a sample comprises:

(1) adding a known quantity of an internal standard compound to a sample containing at least one protein, the internal standard compound producing a detector signal in relation to its concentration and being capable of electrophoretic separation from the protein;

(2) subjecting the sample and the internal standard compound to capillary electrophoresis to separate the protein and the internal standard compound from each other and from other components in the sample;

(3) measuring the detector signal produced by the internal standard compound and a detector signal produced by the protein to determine a ratio of protein signal to internal standard signal; and (4) determining the concentration of the protein in the sample from a standard curve of protein concentration versus the ratio of protein signal to internal standard signal.

Typically, the detector signal is a signal produced by absorption of light in the ultraviolet and/or visible regions of the spectrum.

The protein to be determined can be a protein such as human serum albumin, a myeloma protein, prealbumin, retinol-binding protein, $\alpha_1$-antitrypsin, $\alpha_1$-acid glycoprotein, $\alpha_1$-fetoprotein, haptoglobin, $\alpha_2$-macroglobulin, ceruloplasmin, transferrin, $\beta_2$-microglobulin, C-reactive protein, ferritin, or carcinoembryonic antigen. A typical protein to be determined is human serum albumin.

Typically, the internal standard compound is a benzoic acid substituted with at least one halogen. Preferably, the internal standard compound is a dichlorobenzoic acid, a monochlorobenzoic acid, or a trichlorobenzoic acid. More preferably, the internal standard compound is a dichlorobenzoic acid. A highly preferred internal standard compound is 2,4-dichlorobenzoic acid. Alternatively, the internal standard compound can be a trichlorobenzoic acid, in which case a highly preferred internal standard is 2,4,6-trichlorobenzoic acid.

Preferably, when the internal standard compound is 2,4-dichlorobenzoic acid, the wavelength at which the absorbance of the separated marker protein and the internal standard compound is measured is 214 nm.

In general, the method for determining the total protein concentration in a sample containing at least one protein comprises the steps of:

(1) adding a known quantity of an internal standard compound to a sample containing at least one protein, the internal standard compound producing a detector signal in relation to its concentration and being capable of electrophoretic separation from the protein;

(2) subjecting the sample and the internal standard compound to capillary electrophoresis to separate the protein and the internal standard compound from each other and from other components in the sample;

(3) measuring the detector signal produced by the internal standard compound and a total detector signal produced by all proteins in the sample to determine a ratio of total protein signal to internal standard signal; and (4) determining the total concentration of the protein in the sample from a standard curve of protein concentration versus the ratio of protein signal to internal standard signal.

The internal standard compound is chosen as described above for the method in which the concentration of a particular protein is determined.

BRIEF DESCRIPTION OF THE DRAWINGS

These and other features, aspects, and advantages of the present invention will become better understood with reference to the following description, appended claims, and the accompanying drawings where:

DESCRIPTION

Figure 1:
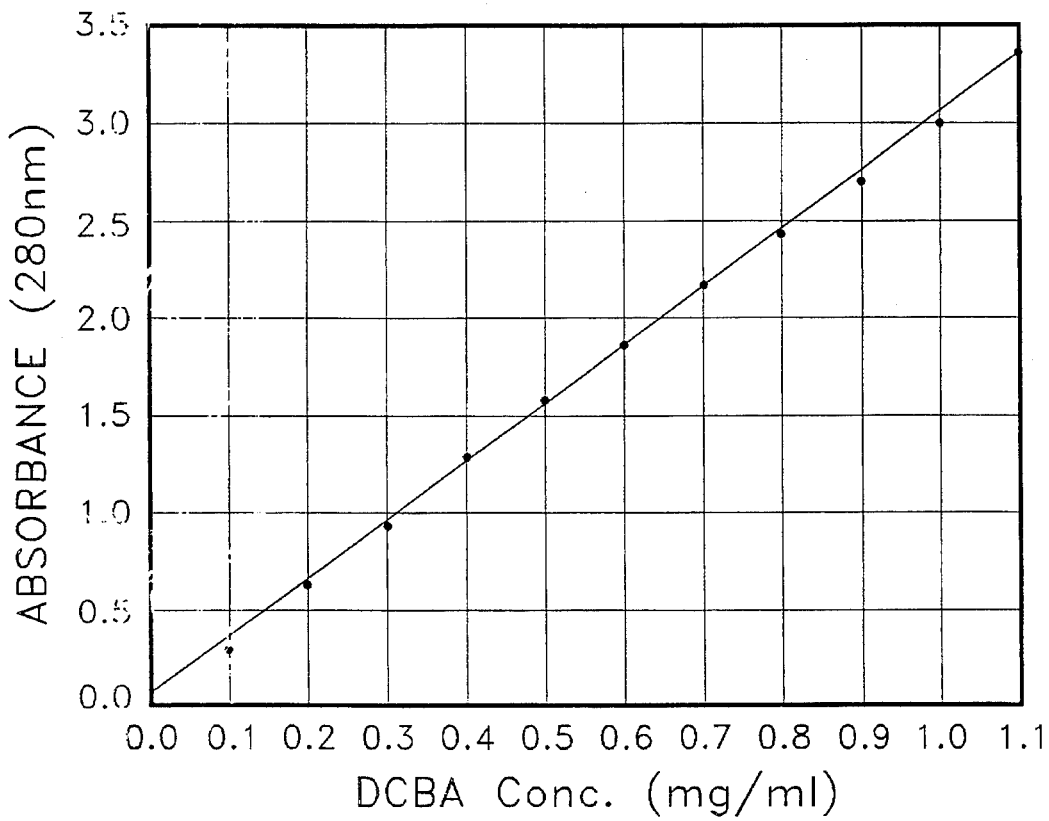
FIG. 1 is a graph of the absorbance of DCBA at 280 nm plotted against the concentration in order to determine the extinction coefficient of DCBA at 280 nm.

We have invented a method that can be used both to determine the quantity of a particular protein in a sample containing a large number of proteins, or to determine the total protein concentration in the sample. This method depends on detection of detector signals produced by proteins separated by capillary electrophoresis, and can be used with a wide variety of samples and a wide variety of marker proteins.

I. GENERAL PRINCIPLES OF PROTEIN DETECTION BY CAPILLARY ELECTROPHORESIS

A. Optical Detection of Macromolecules

A number of detectable signals produced by proteins can be used for their detection subsequent to capillary electrophoresis. These signals include, but are not necessarily limited to, those resulting from absorption of light in the ultraviolet or visible portions of the spectrum, those resulting from fluorescence and/or chemiluminescence, those resulting from refractive index changes, and those resulting from optical rotation such as circular dichroism and optical rotatory dispersion. Typically, absorption of light in the ultraviolet or visible portions of the spectrum is used. Other types of signals, such as those resulting from electrochemical reactions, can also be used.

Most macromolecules are detectable by their absorption of ultraviolet or visible radiation. This absorption is a consequence of the electronic structure of the molecule and yields an absorption spectrum that is specific for each molecule. At any wavelength in dilute solution, the relationship between the intensity of radiation transmitted to the intensity of the incident radiation is governed by the Beer-Lambert Law: $I = I_o \times 10^{-\epsilon lc}$ where $I_o$ is the intensity of the incident radiation and I is the intensity of the radiation transmitted through a cell of thickness 1 cm, containing a solution of concentration c moles/liter. The quantity $\epsilon$ is the extinction coefficient, with the units liter mole$^{-1}$ cm$^{-1}$.

Thus, from a determination of the transmitted radiation and the known intensity of the incident radiation, the concentration of any solute can be determined if the extinction coefficient is known at a particular wavelength, as long as the pathlength is also known. In the typical apparatus for measurement of ultraviolet absorption, which includes the capillary electrophoresis apparatus adapted to the method of the present invention, the thickness of the cell is known from the construction of the cell.

In practice, as discussed below, because the cell thickness is constant, all that is needed is a ratio of the ultraviolet or visible absorption for a particular peak as compared with the absorption at the same wavelength for an internal standard. This ratio is then used in connection with a standard curve of protein concentration versus the ratio of protein ultraviolet absorption to internal standard absorption.

If a sample contains more than one protein species and the protein species are separated from each other, such as by capillary electrophoresis, the total protein concentration in the sample can be determined by integrating the signal obtained from each separated species and then using the total integrated signal obtained from the integration to extrapolate total protein concentration from the standard curve. This yields the total protein concentration in the sample.

1. Detection of Proteins

It is preferred to detect proteins at a wavelength of 214 nm, in the relatively far ultraviolet. At this wavelength, the peptide bonds of the protein molecules absorb. At this wavelength, the extinction coefficient of various proteins are virtually equal; i.e., there is little dependence of the extinction coefficient on any of the following variables: the amino acid composition of the protein, the primary structure of the protein, or the secondary, tertiary, or quaternary structure of the protein. Thus, absorption at this wavelength is an excellent measure of total protein concentration as well as being suitable for the determination of the concentration of an individual protein that is separated from other proteins originally present in a mixture. This is what occurs during capillary electrophoresis, as discussed below.

Alternatively, proteins can be detected by their ultraviolet absorption at a range of wavelengths centered around 280 nm. Absorption in this range of wavelengths is predominantly due to aromatic amino acid residues, particularly tyrosine and tryptophan, and, to a lesser extent, phenylalanine. Accordingly, absorption in this range of wavelengths varies with the amino acid composition of the protein. It also varies with the secondary, tertiary, and quaternary structure of the protein because absorption at this range of wavelengths depends to a substantial degree on the interaction of the residues involved with the solvent. Although it is generally preferred to work at 214 nm, in some cases, it can be desirable to work at longer wavelengths.

2. Detection of Nucleic Acids

Nucleic acids have strong ultraviolet absorptions in the range of 260 nm. This absorption is due to the heterocyclic rings in the nucleotide bases adenine, cytosine, guanine, and thymine (or uracil for RNA). For nucleic acids, the various bases have different absorption maxima and absorption intensity, so the molar absorption intensity varies to a certain extent with base composition. The absorption also varies with the secondary structure of the nucleic acid. Double-stranded nucleic acids such as native DNA have approximately a 30% lower ultraviolet absorption per mole of bases than do single-stranded nucleic acids. This effect is known as hypochromism. However, if the composition and strandedness of the nucleic acid are known, its concentration can be readily determined from the intensity of ultraviolet absorption.

3. Detection of Other Macromolecules

Many prosthetic groups, particularly metal-containing prosthetic groups such as heme derivatives, absorb at a number of wavelengths, particularly at somewhat longer wavelengths. Thus, proteins or polysaccharides bound to components containing such prosthetic groups are detectable by ultraviolet or visible absorption as well. The wavelength involved will depend on the particular metal involved, the structure of the prosthetic group, and its relationship to the rest of the molecule.

B. Capillary Electrophoresis

One preferred method of separating macromolecules, including proteins, is capillary electrophoresis.

1. Basic Principles of Capillary Electrophoresis

Capillary zone electrophoresis (CZE) or capillary electrophoresis, is a technique that employs narrow-bore (10–200 μm inside diameter) capillaries to perform high efficiency separations of both large and small molecules. This separation is facilitated by the use of high voltages, typically 1000 to 30,000 volts, which can generate electroendoosmotic and electrophoretic flow of buffer solutions and ionic species, respectively, within the capillary. The properties of the separation and the ensuing electropherogram have characteristics resembling a cross between traditional polyacrylamide gel electrophoresis (PAGE) and modern high performance liquid chromatography (HPLC).

The force for moving fluid between the sample input and the sample output of the capillary tube is provided by establishing an appropriate voltage between the sample input and the sample output, generating electrophoretic and electroendoosmotic forces as discussed above.

Electroosmosis is a consequence of the surface charge on the wall of the capillary. The fused silica capillaries that are typically used for separations have ionizable silanol groups in contact with the buffer contained within the capillary. The pI of fused silica is about 1.5. The degree of ionization is controlled mainly by the pH of the buffer. Most buffers in which the pH is greater than 1.5 can ionize the capillary wall. The negatively-charged wall attracts positively charged ions from the buffer, creating an electrical double layer. When a voltage is applied across the capillary, cations in the diffuse portion of the double layer migrate in the direction of the cathode carrying water with them. The result is an electroosmotic flow (EOF) of buffer solution in the direction of the negative electrode. In the meantime, the negatively charged analytes, such as proteins, peptides, or other species, in the buffer solution can move against the EOF by electrophoretic migration towards the positive electrodes. Despite the electrophoretic migration of the analytes towards the positive electrode (anode), EOF overwhelms the electrophoretic migration of the analytes, and the analytes migrate toward the negative electrode (cathode). Electrophoretic migration is dependent upon the charge-mass ratio of each molecule, e.g., protein, to be separated. Each molecule possesses a specific charge-mass ratio depending upon its size and amino acid composition and thus migrates with a different speed. In the capillary electrophoresis apparatus, the detection window is arranged in relationship to the point at which the sample enters the electrophoretic field so that the sample is carried to the detection window by EOF. Accordingly, the faster the movement against EOF, the slower a particular protein passes the detection window. This is analogous to a group of very lazy rowboaters who are rowing against the current but are carried downstream faster than they can row. An observer at a point some distance downstream would first be reached by the rower who is rowing the slowest, because his net motion would be the closest to that of the current. The rower who was rowing the most vigorously would in fact arrive last at the observer. Thus, proteins with a high degree of negative charge caused by a high proportion of the negatively charged amino acid residues aspartate and glutamate would arrive at the detection window most slowly. Accordingly, what is measured in capillary electrophoresis is the absorption of the sample passing the detection window as a function of time. This curve yields a series of peaks corresponding to particular protein species. Integrating the area under the peak can therefore be used to quantitate the amount of a particular protein species, and integrating the total area under all peaks of the electropherogram can be used to quantitate the total protein content of the sample.

2. Apparatus for Performing Capillary Electrophoresis

The process of capillary electrophoresis can be performed in any apparatus in which the suitable electrophoretic forces can be generated and in which the peaks resulting can be detected. Typically, the capillary electrophoresis system involves a quartz or fused silica capillary tube of circular cross-section and cylindrical outline, equipped with an ultraviolet emitter and monochromator to select the desired wavelength, as well as a photodetector to detect the ultraviolet light that has passed through the sample. Typical dimensions of the capillary tube are 25 µm inner diameter x 27 cm total length. A suitable capillary tube is that produced by Polymicro Technologies, Phoenix, Ariz. The outer surface of the capillary can be coated with polyimide to protect the capillary from breakage. The optics module and detector can include a UV light source (deuterium lamp) and a 214 nanometer filter in a rotating wheel, as well as a detector that aligns with the aperture of the window. The window can be located at 6.5 cm from the tube outlet. A suitable apparatus for detection of proteins based on ultraviolet absorbance at 214 nm is the Beckman Instruments P/ACE 2000 CE system (Beckman Instruments, Fullerton, Calif.). This system is computer-controlled and can be used with suitable software, such as the CCE software, and an IBM-compatible personal computer such as an IBM PS/2. Other suitable capillary electrophoresis apparatus can also be used.

Although the detected signal has been described for particular wavelengths, in particular 214 nanometers for peptide bonds, it is apparent that the electrophoresis system could operate at many different wavelengths. Signals at multiple discrete wavelengths can be applied to one or more detection paths applied to the tube. Such ranges of wavelengths can be limited or extensive in the electromagnetic (optical) spectrum, as long as the masking constituting the window widths suitably excludes the signal at the selected wavelengths from passing through undesirable sections of the tube wall.

Although the electrophoresis system used for the methods of the present invention has been described with reference to a single capillary electrophoresis unit, it is clear that multiple systems can be used in series or tandem to provide for a continuous monitoring process, such as a time series of protein concentration in a sample. This may be useful when monitoring the development of clinical conditions such as inflammation or immunological reaction.

In other situations, it is possible to have multiple input windows and output windows arranged angularly around the central axis of a capillary tube at selective angles. In different situations, input light of different selected wavelengths can be input into the capillary tube through selected input windows about the axis. Different output windows would then receive the light with the pertinent information about the sample in the tube. This arrangement could, for example, be used to measure both the protein and nucleic acid concentration in a sample relative to two or more internal standards.

II. SPECIFIC METHODS FOR DETERMINING INDIVIDUAL PROTEIN CONCENTRATION AND TOTAL PROTEIN CONCENTRATION

A. Method of Determining Individual Protein Concentration

A method for determining the concentration of a protein constituent in a sample according to the present invention can comprise the steps of:

(1) adding a known quantity of an internal standard compound to a sample containing at least one protein, the internal standard compound selected from the group consisting of benzoic acid substituted with at least one halogen, producing a detector signal in relation to its concentration, and being capable of electrophoretic separation from the protein;

(2) subjecting the sample and the internal standard compound to capillary electrophoresis to separate the protein and the internal standard compound from each other and from other components in the sample;

(3) measuring the detector signal produced by the internal standard compound and a detector signal produced by the protein to determine a ratio of protein signal to internal standard signal; and (4) determining the concentration of the protein in the sample from a standard curve of protein concentration versus the ratio of protein signal to internal standard signal.

Typically, the detector signal is an electromagnetic radiative signal. Typically, the electromagnetic radiative signal is one produced by absorption of light in the ultraviolet and/or visible regions of the spectrum. However, other detectable electromagnetic radiative signals can be used, as well as other signals related to protein concentration such as those resulting from electrochemical reactions.

To prepare the standard curve of protein concentration versus the ratio of protein signal to internal standard signal, it is not necessary to know either the absolute concentration of the internal standard used or the molar absorptivity of the internal standard at the wavelength used. It is only necessary to know the relative concentration of the internal standard used or to use the same concentration of the internal standard for all points on the standard curve. This relative concentration can be determined spectrophotometrically.

However, to establish the standard curve, it is necessary to know the actual protein concentration of the protein samples assayed to form the curve. Because, as stated above, the absorbance of proteins at 214 nanometers varies very little with protein composition or structure, if that wavelength is used, the molar absorptivity for a typical protein such as human serum albumin can be used for other proteins, with negligible error. Alternatively, any protein can be purified to substantial homogeneity and quantitated by procedures such as the biuret reaction, Kjeldahl nitrogen determination, the Lowry protein assay, or dye-binding assays, so that solutions of the protein of known concentration can be prepared.

The protein to be detected can be any protein. For example, the protein to be detected can be human serum albumin, a myeloma protein, prealbumin, retinol-binding protein, $\alpha_1$-antitrypsin, $\alpha_1$-acid glycoprotein, $\alpha_1$-fetoprotein, haptoglobin, $\alpha_2$-macroglobulin, ceruloplasmin, transferrin, $\beta_2$-microglobulin, C-reactive protein, ferritin, or carcinoembryonic antigen. Other proteins can similarly be determined. A typical protein to be detected is human serum albumin.

Typically, the benzoic acid substituted with at least one halogen is a monochlorobenzoic acid, a C) dichlorobenzoic acid, or a trichlorobenzoic acid. Preferably, if absorbance measurements are made at 214 nm, the benzoic acid substituted with at least one halogen is a dichlorobenzoic acid. More preferably, the internal standard compound is 2,4-dichlorobenzoic acid. Alternatively, if absorbance measurements are made at 214 nm, the benzoic acid substituted with at least one halogen can be a trichlorobenzoic acid, preferably 2,4,6-trichlorobenzoic acid.

As discussed below in Example 18, one criterion for selecting an internal standard is the degree of separation between the internal standard and the protein components that results after capillary electrophoresis of samples containing the internal standard. This degree of separation can vary with the pH used for electrophoresis. The degree of separation between prealbumin and 2,4-dichlorobenzoic acid is greater than the degree of separation between prealbumin and 2,4,6-trichlorobenzoic acid at pH values greater than 10.3. Thus, if electrophoresis is carried out at pH values greater than 10.3, the use of 2,4-dichlorobenzoic acid is preferred.

If measurements are made at wavelengths other than 214 nanometers, the internal standard compound used is one that has significant absorption at that wavelength and is readily separable from any proteins in the sample. Such a marker compound could be an aromatic or heterocyclic compound with the desired absorption. Data for absorption for organic compounds is found, for example, in publications from the Sadtler Research Laboratories, as well as in the "Atlas of Spectral Data and Physical Constants for Organic Compounds" CRC Press, Cleveland, Ohio, and in "Organic Electronic Spectral Data" published by Interscience, New York. In general, most heterocyclic and aromatic compounds are readily separable from proteins because of their different charge/mass ratio.

Once the standard curve has been prepared, the quantity of the protein can be readily determined by integrating the area under the peak for the protein to be determined on the electropherogram, computing the ratio of the total electromagnetic radiative signal resulting from the peak with the signal for the internal standard, and determining the quantity of the protein from the standard curve.

This method can be used for any protein-containing sample including both biological and non-biological fluids. It can be used, for example, for plasma, serum, cerebrospinal fluid, urine, lymph, seminal or vaginal secretions, sputum, products of gastric, bronchial, or pulmonary lavage, or other fluids encountered in clinical practice. Similarly, the method can be used on non-biological samples including environmental waste and other samples that may contain proteins as evidence of microbial growth or contamination.

In some cases, it may be desirable to perform a preliminary extraction or purification of the sample by removing potentially interfering substances such as lipids or other substances. Such procedures are well known in the art and need not be described here further.

B. Method of Determining Total Protein Concentration

The present invention also encompasses a method of determining the total protein concentration in a sample. The method involves determining the total protein concentration in the sample by integrating the detector signal from each separated protein peak in the sample, and then using the total signal to determine the protein concentration. As used herein, the term "protein concentration" also encompasses "protein content," that is, the total mass of protein in the sample and not merely the mass per unit volume. If the volume of the sample is known, the protein content can be calculated simply by multiplying the protein concentration by the volume. In some cases, however, such as with originally solid or partially solid samples or samples produced by extraction of solid material, the volume of the sample may not be completely known and results are then reported in terms of protein content.

In general, the method comprises the steps of:

(1) adding a known quantity of an internal standard compound to a sample containing at least one protein, the internal standard compound producing a detector signal in relation to its concentration and being capable of electrophoretic separation from the protein;

(2) subjecting the sample and the internal standard compound to capillary electrophoresis to separate the protein and the internal standard compound from each other and from other components in the sample;

(3) measuring the detector signal produced by the internal standard compound and a total detector signal produced by all proteins in the sample to determine a ratio of total protein signal to internal standard signal; and (4) determining the total concentration of the protein in the sample from a standard curve of protein concentration versus the ratio of total protein signal to internal standard signal.

In this method, the step of electrophoresis separates the internal standard compound from the proteins in the sample.

Once a ratio of the total protein signal to the internal standard signal is obtained, the total protein concentration can be determined from the standard curve in the same way that the concentration of a single protein is determined, as described above.

This method has an extremely wide dynamic range, and can be used to determine total protein concentration over broad ranges.

The invention is illustrated by the following Examples. The examples are for illustrative purposes only and are not intended to limit the invention.

EXAMPLES

Example 1

Standardization of Internal Standard Solution

To insure that reproducible results would be obtained, the preparation method for the internal standard solution was standardized. A quantity of 2,4-dichlorobenzoic acid (DCBA) (100 mg) was weighed out and dissolved in 0.2 ml dimethylformamide (DMF) to make a 500 mg/ml stock solution. Further dilutions were made with DMF to make solutions with DCBA concentrations ranging from 0.1 to 0.5 mg/ml. Ultraviolet spectra from 200 nanometers to 300 nanometers were taken for these solutions and the absorbance values at 280 nanometers were recorded. FIG. 1 shows the absorbance value of DCBA was linearly proportional to the concentration of the compound; i.e., the compound obeys Beer's law. Based on this observation, all DCBA stock solutions used in these examples were made volumetrically so that all solutions diluted at 1:1000 gave an absorbance value of 1.59 at 280 nanometers. Note that the actual absorbance measurements after electrophoresis were made at 214 nanometers. The standardization procedure was intended to avoid experimental errors that might be produced from the weighing of DCBA on the balance.

Example 2

Determination of the Extinction Coefficients of 2, 4-Dichlorobenzoic Acid (DCBA) and 2, 4, 6-Trichlorobenzoic Acid (TCBA) at 280 nm and 214 nm In order that relative concentrations of internal standards could be determined reproducibly, the extinction coefficients of DCBA and TCBA were determined at 280 nm and 214 nm for botch compounds. The method for DCBA and for TCBA was identical. For DCBA, an exact amount of DCBA was weighed out and dissolved in dimethylformamide (DMF) to make a concentration of 10 mg/ml. Serial dilutions were made from the solution at 10 mg/ml with DMF to generate a series of standard DCBA solutions with concentrations between 0.1 mg/ml and 1.0 mg/ml. Absorbance values at 280 nm were recorded against DMF for these solutions and plotted against the respective concentrations. These results are shown in FIG. 1. Linear regression analysis of the data resulted in the following equation: $Y=2.97X+0.059$, where Y is the absorbance and X is the concentration of DCBA in mg/ml. For all subsequent experiments, the concentration of DCBA was calculated by using the equation $X=(Y-0.059)/2.97$. Similar results were obtained for TCBA at 280 and 214 nm.

Example 3

Determination of Extinction Coefficients of Human Serum Albumin and Human Immunoglobulin G at 214 nm As indicated above, the ultraviolet absorption of proteins at 280 nm is predominantly attributable to the aromatic amino acid residues, particularly tyrosine and tryptophan, as well as phenylalanine. The absorbance at 280 nm varies from protein to protein depending on the composition of the particular protein and the abundance of the UV-absorbing amino acid residues. On the other hand, the absorption of proteins at 214 nm is predominantly attributable to the peptide bond. The absorbance at this wavelength is nearly linearly dependent on the number of peptide bonds, which in turn is proportional to the mass of the protein regardless of the particular protein species involved or its composition. Another advantage of protein detection at 214 nm is that the absorptivity of the protein is usually greater at 214 nm than at 280 nm.

Accordingly, the extinction coefficients of albumin and human immunoglobulin G were measured at 214 nm. Albumin and immunoglobulin G solutions were made in ICS diluent (75 mM sodium chloride, 20 mM potassium phosphate, pH 7.0). Concentrations of the proteins were measured by ultraviolet absorbance at 280 nm using extinction coefficients of 0.58 and 1.38 for 1 mg/ml solutions of albumin and immunoglobulin G respectively. The absorbance value for albumin and immunoglobulin G at 214 nm was measured for a 1 mg/ml solution and was found to be 14.2 for albumin and 14.7 for immunoglobulin G. These results also showed that the detection sensitivity at 214 nm was about 25 (14.2/0.58) times that at 280 nm for albumin, and for immunoglobulin G, the detection sensitivity was about 11 times higher (14.7/1.38) at 214 nm.

Example 4

Establishment of a Conversion Factor for Calculating Albumin Concentration from Electropherograms Using Peak Area Ratio of Albumin to DCBA A series of albumin solutions was made, and the albumin concentration of each solution was determined spectrophotometrically based on an extinction coefficient of 0.58 for a 1 mg/ml solution at 280 nm using a 1 cm light path. A DCBA stock solution was made at such a concentration that a 1:1000 dilution would give an absorbance value of 1.59 at 280 nm. Each albumin solution (30 μl) was mixed with 270 μl of the diluted DCBA stock solution so that the final concentration of albumin in the stock solution ranged from 2 mg/ml to 8 mg/ml.

Each mixture was subjected to capillary electrophoresis by the following procedure:

Apparatus

A Beckman P/ACE 2000 CE system was used with Beckman CCE software, a modification of "System Gold", which was controlled by an IBM PS/2 PC. Electrophoreses were performed in a untreated fused silica capillary tube. The outer surface of the capillary was coated with polyimide to protect the capillary from breakage (Polymicro Technologies, Inc., Phoenix, Ariz.). The optics module and detector included a UV light source (deuterium lamp) and a 214 nanometer filter in a rotating wheel, as well as a detector that aligned with the aperture of the window. The window was located at 6.5 cm from the tube outlet.

Capillary Electrophoresis Reagents

Running buffer was prepared as follows: 9.27 g of boric acid was weighed out and dissolved into 800 ml of deionized water. A pH meter was calibrated with two standard pH solutions at pH 7.0 and 10.0, and the boric acid solution was then adjusted to a pH of 10.2 with 1 N NaOH. The boric acid solution was then adjusted to a final volume of 1000 ml using volumetric apparatus and filtered through a 0.22 μm membrane (Corning, Corning, N.Y., Filter Catalog Number 25952) and stored at room temperature in a glass bottle.

DCBA-containing sample diluent was prepared as follows: 100 mg of 2,4-dichlorobenzoic acid (Eastman Kodak, Rochester, N.Y.) was dissolved in 200 μl of dimethylformamide (J. T. Baker, Phillipsburg, N.J.). This solution was vortexed until the DCBA was completely dissolved. A 40-μl volume of the DCBA solution was then added into 100 ml of ICS diluent as described above. The DCBA-containing sample diluent was filtered through an 0.22 μl membrane and stored at room temperature in a glass bottle.

The rinse solution A was 1 N NaOH. The rinse solution B was deionized water.

Procedure for Capillary Electrophoresis

The serum was collected from a blood sample as described above and diluted to a final total volume of 300 μl with one part of serum being diluted with 9 parts of DCBA-containing sample diluent. The vial was then placed on the sample tray of the electrophoresis apparatus. The parameters for electrophoresis was set as follows: The capillary was 27 μm×20 cm. The wavelength for measurements was 214 nm. The temperature was 24° C. The injection mode was pressure injection for 10 seconds. The separation voltage was 10 kilovolts. The separation time was 7 minutes. The current was close to 20 μA.

The operating sequence was set as follows: The column was rinsed with running buffer for 1.5 minutes. The column was equilibrated with running buffer for 0.5 minutes. Pressure injection was performed for ten seconds as indicated, and the separation was performed at 10 kilovolts voltage for 7 minutes. The column was then rinsed with rinse solution A for 1 minute, and then with rinse solution B for 1 minute.

Column maintenance was as follows: At the beginning of each day, the column was rinsed with rinse solution A for 1 minute, rinse solution B for 5 minutes, and running buffer for 15 minutes. At the end of each day, the column was rinsed with rinse solution A for 1 minute and rinse solution B for 5 minutes.

For data analysis, the CCE software was used to adjust the baseline, normalize the absorbance of the internal standard, and normalize migration time by two internal standards. The "delimit" integrator function was then used to calculate the relative area under the peaks and ratio of the protein peak area to that of the internal standard peak area.

Figure 2:
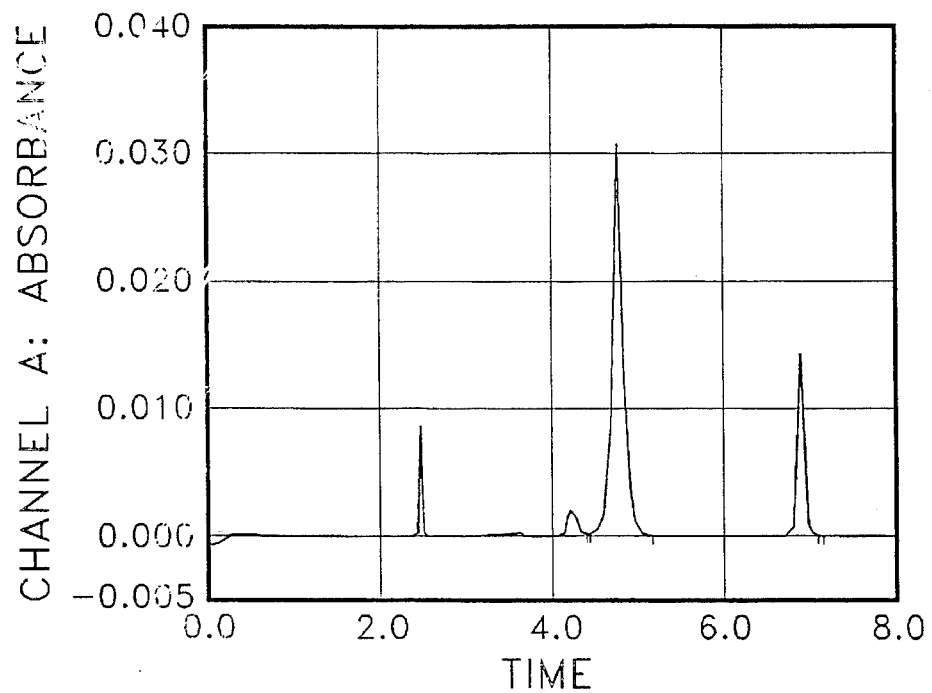
FIG. 2 is an electropherogram with absorbance measured at 214 nm showing the separation of albumin from DCBA.
Figure 3:
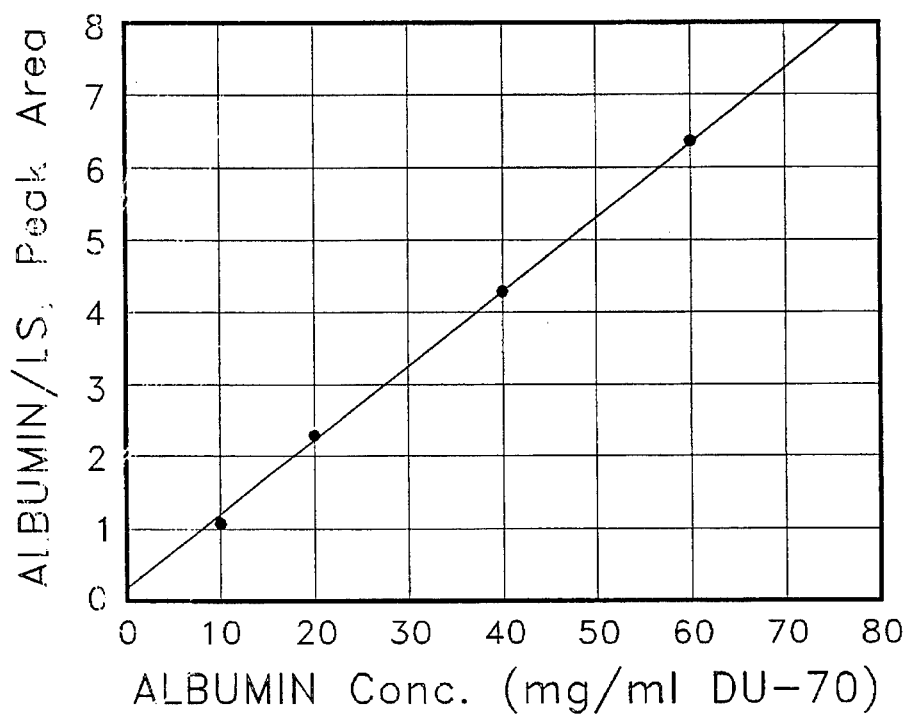
FIG. 3 is a graph showing a standard curve generated by plotting the area of the capillary electrophoresis peak of albumin in buffer divided by the area of an internal standard peak against the human serum albumin concentration.

A typical electropherogram is shown in FIG. 2. The peak area ratio of albumin to DCBA was calculated. A linear relationship was observed between the ratio and the concentration of albumin (FIG. 3). Using linear regression analysis, the slope was found to be 0.1029 for a 1.0 mg/ml albumin solution. The result of this regression analysis was then used as a conversion factor for calculating albumin concentration in further experiments.

Example 5

Determination of Serum Albumin Concentration Using Spiked Human Serum Samples

Figure 4:
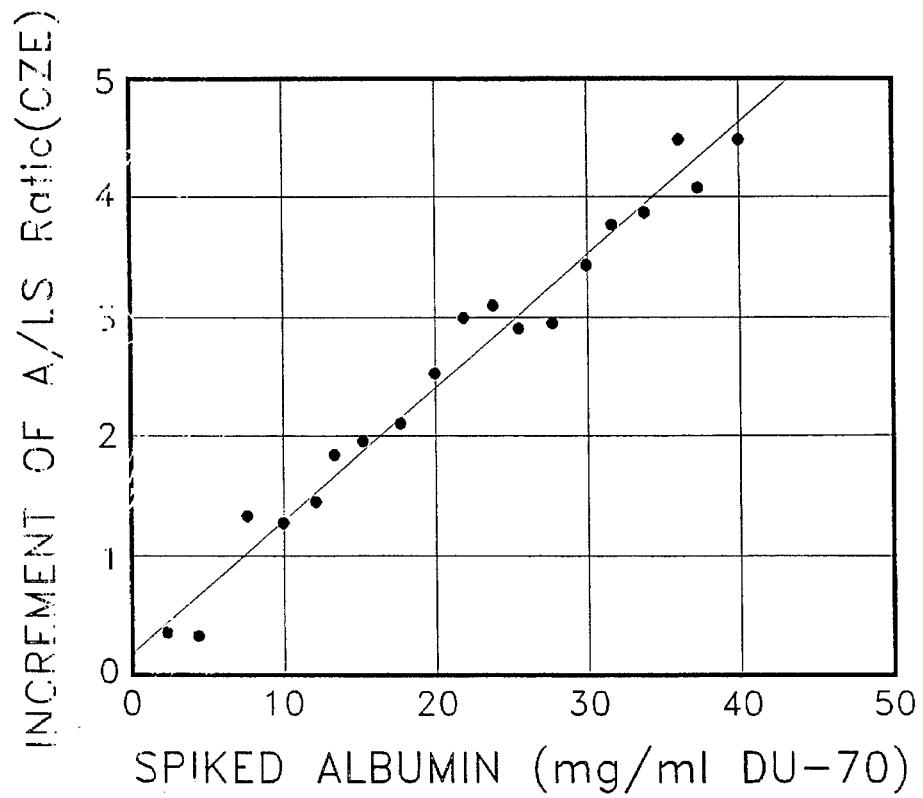
FIG. 4 is a graph showing a standard curve generated by plotting the area of the capillary electrophoresis peak of albumin in spiked serum samples divided by the area of an internal standard peak against the albumin concentration after correcting for the endogenous albumin in the sample.

In order to see whether any component of serum might have an effect on the assay, the same experiments were performed by using human serum spiked with purified human serum albumin. Because native unstripped human serum was used in these experiments, a background peak appeared in the zero dose-spiked standard solution due to endogenous albumin. The peak area ratio at zero dose was subtracted from the ratios of all albumin concentrations. The resulting ratio increments were plotted against the concentrations as shown in FIG. 4. Linear regression analysis of this data produced a straight line represented by the following equation: $Y=0.112X+0.128$. Therefore, the concentration of albumin in an unknown sample can be determined by the equation $X=(Y-0.128)/0.112$. These experiments indicated that the addition of serum has little or no effect on the assay.

Example 6

Quantitation of Human Serum Albumin in Blood Samples

Human blood samples were collected with a Vacutainer Red Top Apparatus (Becton-Dickinson, Franklin Lakes, N.J.). After the blood coagulated, the serum was collected and diluted with sample diluent (Beckman Instruments, Inc., Fullerton, Calif., ICS diluent, containing 75 mM sodium chloride, 20 mM potassium phosphate, pH 7.0).

Capillary electrophoresis was carried out as described above using a DCBA internal standard. The same linear relationship was observed between the albumin concentration and the peak area ratio of albumin to DCBA in serum as was observed in the calibration run using only albumin and DCBA (FIG. 3), indicating that the presence of other components of serum did not interfere with the assay.

Example 7

Figure 5:
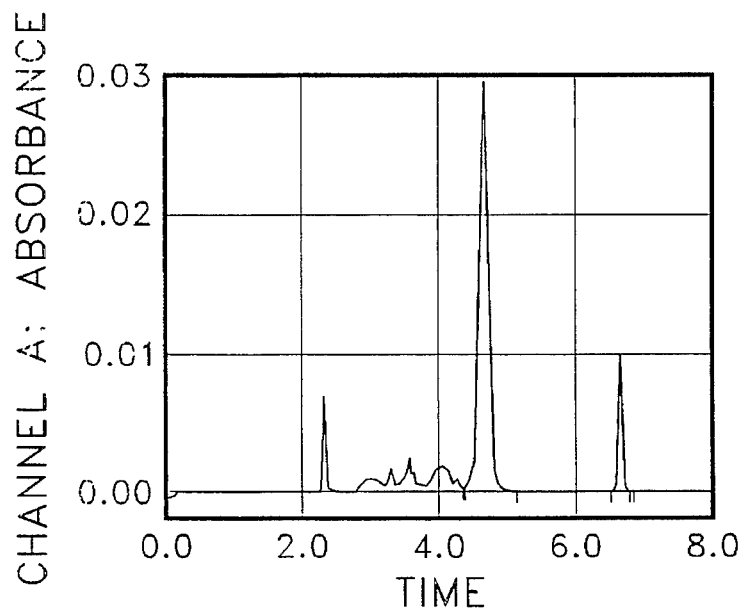
FIG. 5 is an electropherogram similar to that shown in FIG. 2, except that the sample was human serum spiked with a known concentration of human serum albumin.
Figure 6:
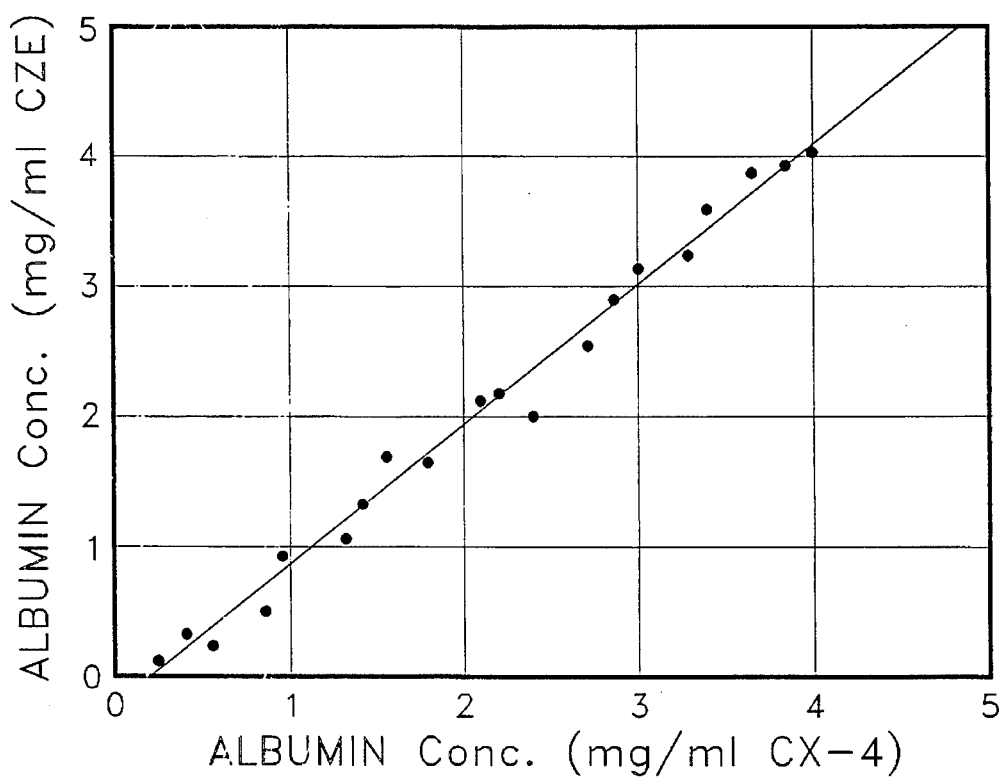
FIG. 6 is a graph showing the correlation of results of albumin concentration obtained with the method of the present invention and with the Synchron method.
Figure 7:
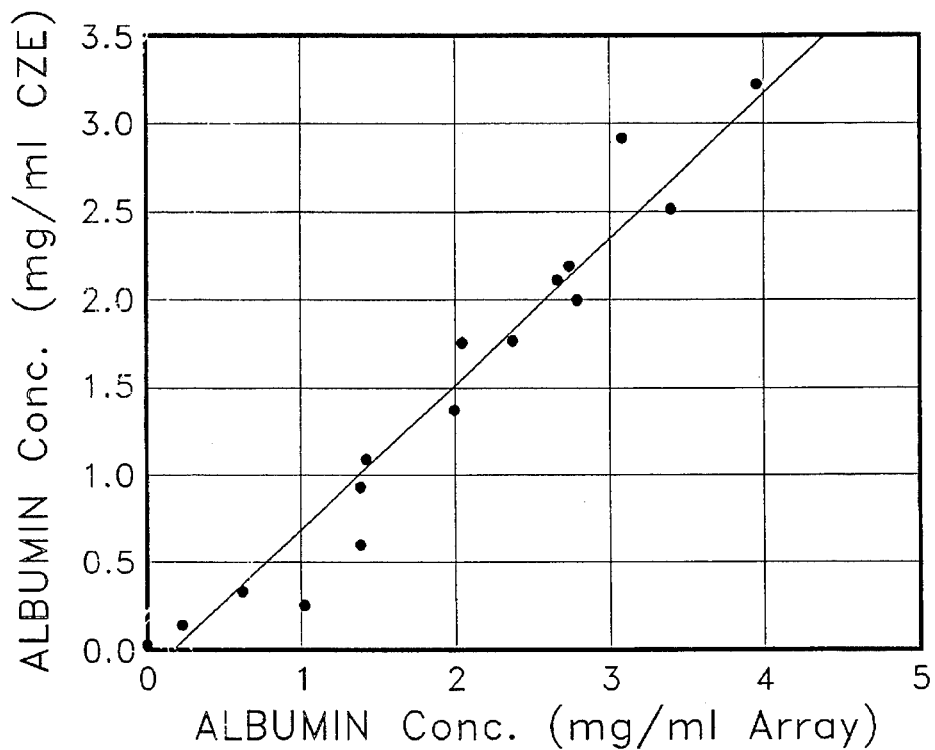
FIG. 7 is a similar graph showing the correlation of results of albumin concentration obtained with the method of the present invention and with the Array method.

Correlation Between the Method of the Present Invention and Other Methods for Determining Albumin Concentration The reliability of the method of the present invention was tested by determining the correlation between results obtained with the method and those obtained with the Synchron (Beckman Instruments, Fullerton, Calif.) method and the Array (Beckman Instruments) method. Varying amounts of serum albumin were spiked in the human serum samples to make specimens with albumin concentration ranging from 0.2 mg/ml up to 4.0 mg/ml. The samples were assayed for albumin concentration by the three methods: Synchron, Array, and the capillary electrophoresis method of the present invention. A typical electropherogram of the serum sample by capillary electrophoresis is shown in FIG. 5. The concentration of albumin in each sample was calculated by taking the peak area ratio of albumin to DCBA, dividing by the conversion factor, and extrapolated from the standard curve, and then compared with the results obtained by the other methods. Tables 1 and 2 (FIGS. 6 and 7) show that between the capillary electrophoresis method of the present invention and Synchron, the correlation coefficient is 0.9939 with the slope of 1.055, and that between the method of the present invention and Array, the correlation coefficient is 0.9786 with the slope of 0.899. These results indicate a high degree of correlation between the results obtained with the method of the present invention and results obtained with other well-established methods.

TABLE 1

CORRELATION BETWEEN RESULTS FROM CAPILLARY ELECTROPHORESIS AND RESULTS FROM SYNCHRON SYSTEM FOR CONCENTRATION OF ALBUMIN SPIKED IN HUMAN SERUM
Albumin Concentration mg/ml

| By Capillary Electrophoresis | By Synchron |
| --- | --- |
| 0 | 0 |
| 0.28 | 0.20 |
| 0.25 | 0.35 |
| 0.76 | 0.5 |
| 1.25 | 0.82 |
| 1.16 | 0.94 |
| 1.34 | 1.23 |
| 1.7 | 1.36 |
| 1.86 | 1.51 |
| 2.0 | 1.79 |
| 2.35 | 2.06 |
| 2.86 | 2.15 |
| 3.0 | 2.43 |
| 2.8 | 2.67 |
| 2.83 | 2.81 |
| 3.21 | 3.0 |
| 3.57 | 3.24 |
| 3.69 | 3.39 |
| 4.23 | 3.6 |
| 3.9 | 3.81 |
| 4.25 | 4.0 |

TABLE 2

CORRELATION BETWEEN RESULTS FROM CAPILLARY ELECTROPHORESIS AND RESULTS FROM ARRAY SYSTEM FOR CONCENTRATION OF ALBUMIN SPIKED IN HUMAN SERUM
Albumin Concentration mg/ml

| By Capillary Electrophoresis | By Array |
| --- | --- |
| 0 | 0 |
| 0.28 | 0.22 |
| 0.25 | 0.62 |
| 0.76 | 1.04 |
| 1.25 | 1.41 |
| 1.16 | 1.46 |
| 1.34 | 1.50 |
| 1.7 | 2.0 |
| 1.86 | 2.04 |

TABLE 2-continued

CORRELATION BETWEEN RESULTS FROM CAPILLARY
ELECTROPHORESIS AND RESULTS FROM ARRAY
SYSTEM FOR CONCENTRATION OF ALBUMIN SPIKED
IN HUMAN SERUM
Albumin Concentration mg/ml

| By Capillary Electrophoresis | By Array |
| --- | --- |
| 2.0 | 2.37 |
| 2.35 | 2.72 |
| 2.86 | 2.78 |
| 3.0 | 2.87 |
| 2.80 | 3.43 |
| 2.83 | 3.12 |
| 3.21 | 3.96 |

Example 8

Determination of Total Protein Concentration in Serum

Figure 8:
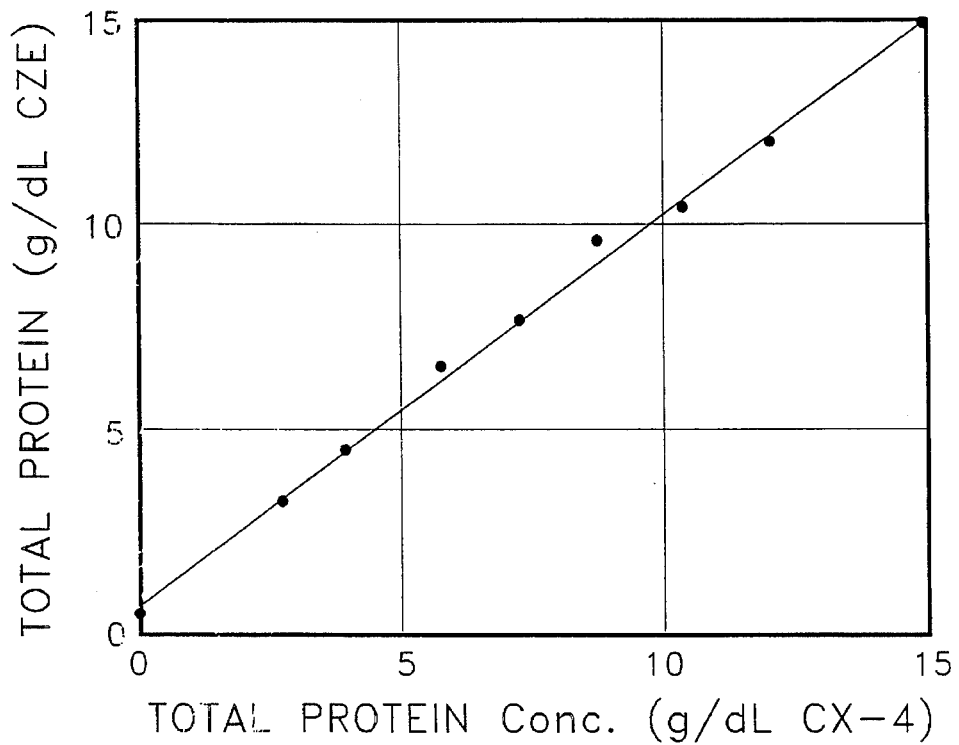
FIG. 8 is another similar graph showing the correlation of results of total protein concentration in serum samples obtained with the method of the present invention and with the Synchron method.

From the electropherogram, the total signal resulting from absorbance of the electrophoresed proteins at 214 nm was determined, and the total protein concentration of the sample was then determined by using the total protein signal. The total protein of the sample was then calculated by calculating the ratio of the total protein signal to the internal standard signal, and then determining the total protein concentration from the standard curve that related the ratio of protein signal to the internal standard signal to the protein concentration. The total protein concentration of each sample was also measured with the Synchron method. Table 3 and FIG. 8 show the correlation results between the two methods. A correlation coefficient is 0.9977 with a slope of 0.94 was obtained. Again, this indicates a high degree of correlation between the methods.

TABLE 3

CORRELATION BETWEEN PROTEIN CONCENTRATION
DETERMINED BY CZE AND BY SYNCHRON
ASSAY METHOD

| Protein Concentration, mg/ml (CZE) | Protein Concentration, mg/ml (Synchron) |
| --- | --- |
| 2.44 | 2.5 |
| 2.85 | 2.6 |
| 2.92 | 2.8 |
| 3.25 | 3.65 |
| 6.79 | 7.35 |

Example 9

Comparison of Dichlorobenzoic Acid and Trichlorobenzoic Acid as Internal Standards at Varying pH's The internal standards 2,4-dichlorobenzoic acid (DCBA) and 2,4,6-trichlorobenzoic acid (TCBA) were compared in capillary electrophoresis of serum samples in order to determine the separation between the serum protein components and the internal standards as a function of the pH at which the electrophoresis was carried out.

For DCBA, electrophoresis was carried out essentially as described above on the Beckman P/ACE 2000 system at 24° C. The capillary used was 25 μm in diameter and 20 cm in effective length. The detection wavelength was 214 nm. The separation voltage was 10 kv, and the separation time was 8 minutes. Sample injection was for 10 seconds in the pressure injection mode. The serum sample was diluted 10-fold with Beckman ICS diluent, containing 0.04% (v/v) dimethylformamide, 0.02% (w/v) DCBA, and 1% polyoxyethylene-9-lauryl ether (Thesit, Sigma, St. Louis, Mo.). The electrophoresis buffer was 150 mM boric acid, adjusted to a pH of from 9.5 to 10.5.

Figure 9:
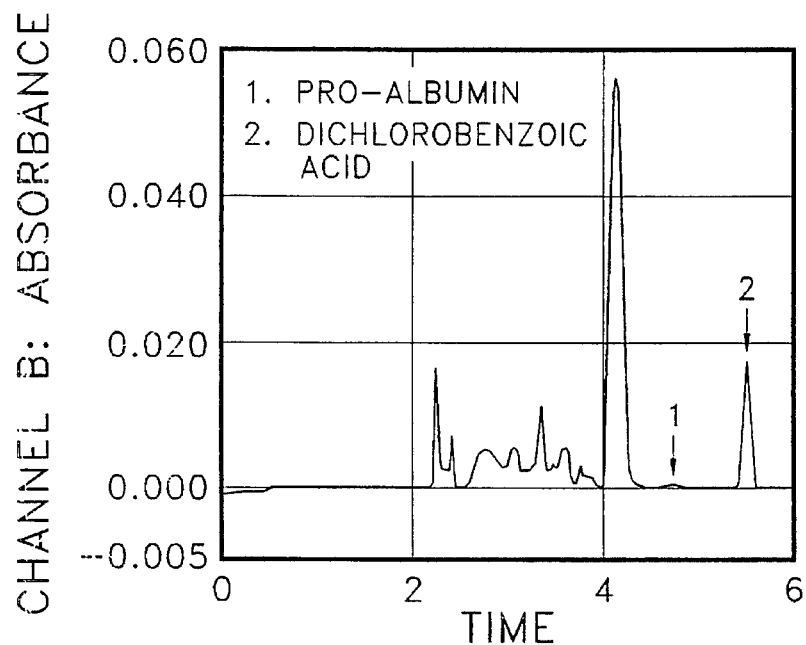
FIG. 9 is an electropherogram showing the separation of serum components, including prealbumin, from DCBA at pH 10.2.

The migration times in minutes for the prealbumin and the DCBA are shown in Table 4. The electropherogram resulting at pH 10.2 for DCBA is shown in FIG. 9.

Figure 10:
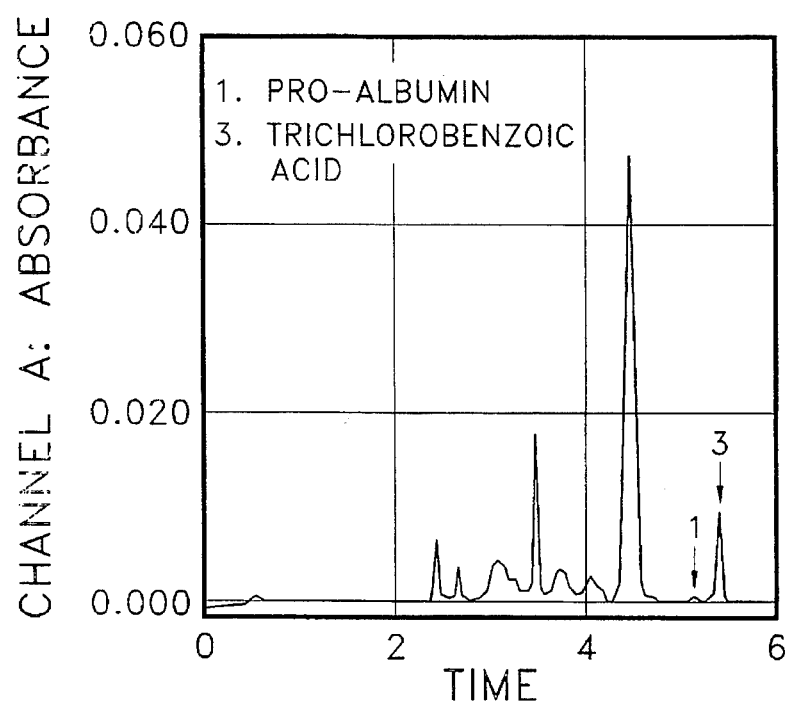
FIG. 10 is an electropherogram showing the separation of serum components, including prealbumin, from trichlorobenzoic acid (TCBA) at pH 10.2.

Electrophoresis was carried out with the same way using TCBA as the internal standard, at pH values of from 10.0 to 10.3. The migration times in minutes for the prealbumin and the TCBA are shown in Table 5. The electropherogram resulting at pH 10.2 for TCBA is shown in FIG. 10. The results indicate that at pH values between 9.5 and 10.3, either DCBA or TCBA is an effective internal standard, while at pH values greater than 10.3, the resolution between prealbumin and TCBA is reduced (data not shown) and the resolution between prealbumin and DCBA is good. Therefore, at pH values greater than 10.3, DCBA is preferred as the internal standard. If prealbumin is not of interest or is not present in the sample, both DCBA and TCBA can be used as internal standards.

TABLE 4

SEPARATION OF PREALBUMIN FROM DICHLOROBEN-
ZOIC ACID BY CAPILLARY ELECTROPHORESIS AT
VARIOUS PH VALUES

| pH | Migration Prealbumin | Time, min Dichlorobenzoic Acid |
| --- | --- | --- |
| 9.5 | 4.47 | 5.39 |
| 9.6 | 4.74 | 5.81 |
| 9.7 | 4.44 | 5.31 |
| 9.8 | 4.70 | 5.73 |
| 9.9 | 4.99 | 6.05 |
| 10.0 | 4.94 | 5.89 |
| 10.1 | 5.0 | 5.81 |
| 10.2 | 4.87 | 5.57 |
| 10.3 | 5.19 | 5.95 |
| 10.4 | 5.84 | 6.60 |
| 10.5 | 5.44 | 6.0 |

TABLE 5

SEPARATION OF PREALBUMIN FROM TRICHLORO-
BENZOIC ACID BY CAPILLARY ELECTROPHORESIS AT
VARIOUS PH VALUES

| pH | Migration Prealbumin | Time, min Trichlorobenzoic Acid |
| --- | --- | --- |
| 10.0 | 4.60 | 4.88 |
| 10.1 | 4.52 | 4.78 |
| 10.2 | 4.60 | 4.75 |
| 10.3 | 4.21 | 4.55 |

Example 11

Quantitation of Microalbumin in Diabetic Urine Samples by Capillary Zone Electrophoresis The method of the present invention was used to quantitate microalbumin or low concentrations of albumin in diabetic urine samples. The method as described above for serum was used, with TCBA as the internal standard. A series of standard serum albumin solutions was used to spike normal urine, previously filtered through a Bio-Gel™ P6 gel filtration column (Bio-Rad, Richmond, Calif.) to make urine samples with varying albumin concentrations between 20 μg/ml and 640 μg/ml. The urine samples were then analyzed by capillary electrophoresis as described above.

Figure 11:
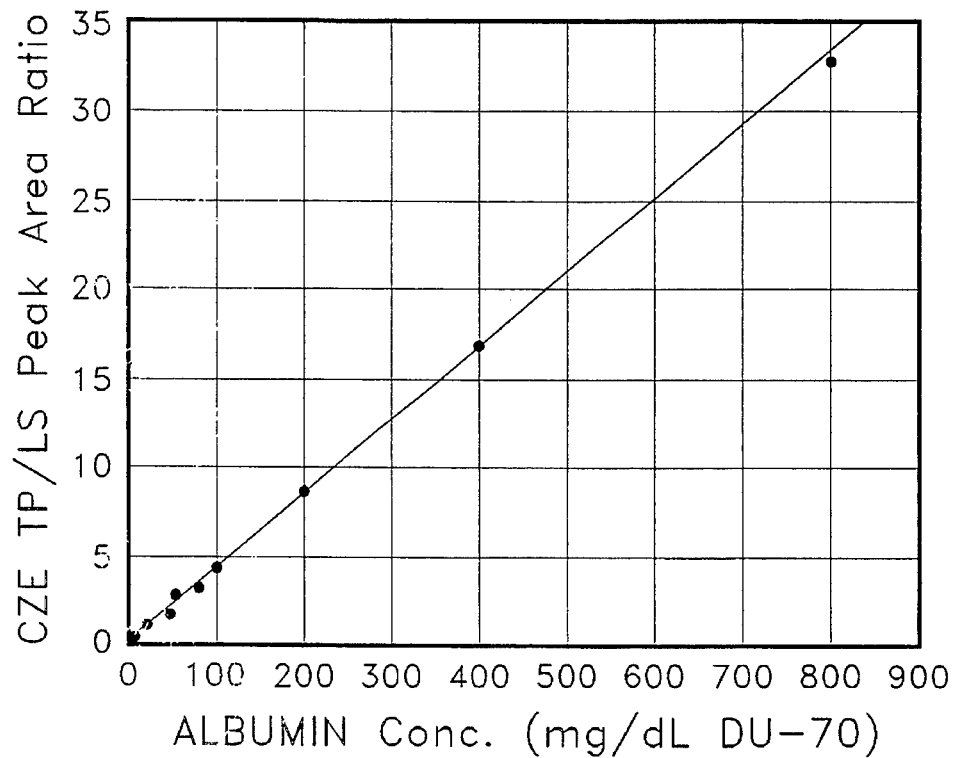
FIG. 11 is a standard curve graph for the determination of albumin in urine similar to that of FIG. 3, except that the urine samples used had been treated by passage through a gel filtration column to remove interfering small molecules.

The results are shown in FIG. 11. A straight line was obtained which is represented by the following equation: Y=0.0041X−0.26. From this equation, for an unknown sample, the concentration of urine albumin can be extrapolated from the peak area ratio of albumin to internal standard in the electropherogram: X (μg/ml)= (Y−0.26)/0.041. At the lowest concentration, 20 μg/ml, a signal to noise ratio of greater than 2 was obtained. This represents about the lowest reliably detectable concentration. The clinically significant concentration range of urine microalbumin for diabetic patients is 20 μg/ml to 200 μg/ml. Therefore, the method can be used to assist the diagnosis of diabetic patients.

Figure 12:
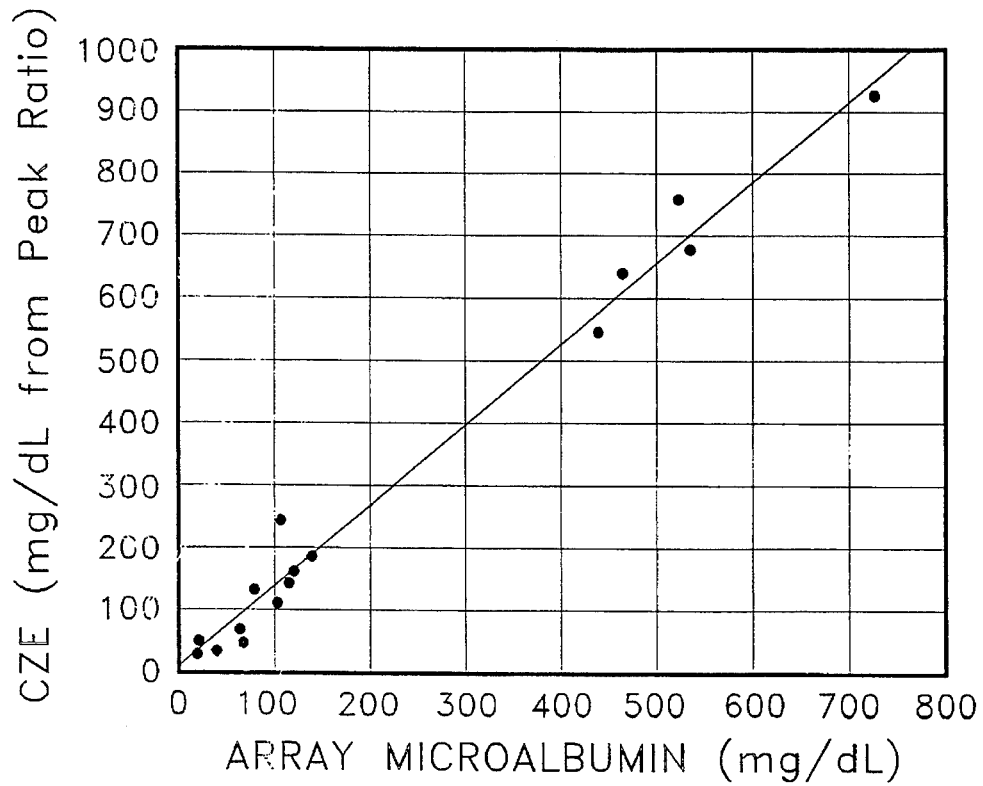
FIG. 12 is a similar graph showing the correlation of results of albumin in human urine obtained with the method of the present invention and with the Array method.

Sixteen urine samples were analyzed from microalbumin using the method of the present invention and the Array system. The results are shown in FIG. 12. Linear regression of the data showed a correlation coefficient of 0.9916 with a slope of 1.3 and an intercept of 7,927. The lower albumin recovery obtained with the Array method was probably due to the difference in the method for albumin concentration determination in the calibrators between the method of the present invention and the Array.

Example 11

Analysis of Urine Samples for Albumin and Total Protein

Several urine samples were analyzed for albumin by the capillary electrophoresis method of the present invention and by the Array 360 (Beckman Instruments, Fullerton, Calif.) system.

The results are shown in FIG. 12. Linear regression analysis of the data produced a straight line with a correlation coefficient of 0.9916, a slope of 1.3, and an intercept of 7.9. These results showed a 30% higher albumin recovery with the capillary electrophoresis method than with the Array method.

Figure 13:
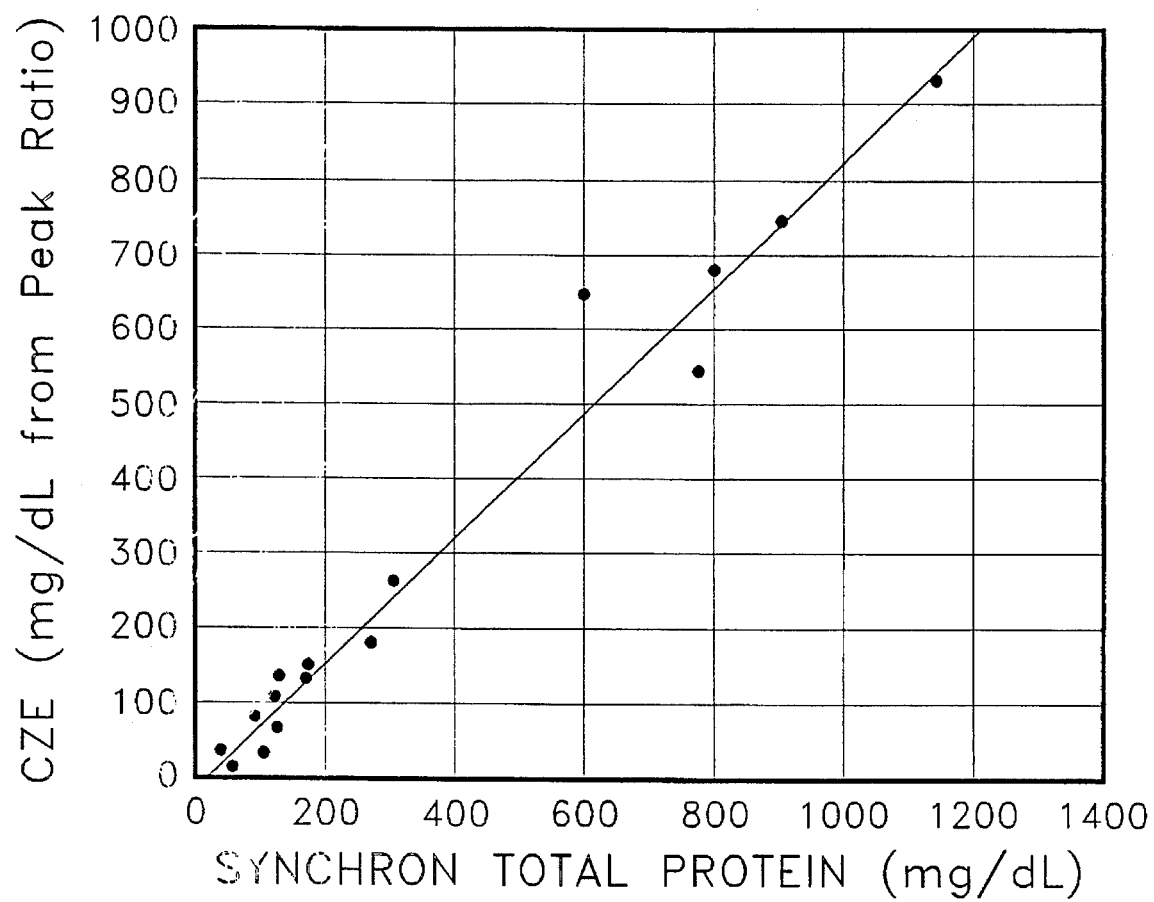
FIG. 13 is a similar graph showing the correlation of results of total protein in human urine obtained with the method of the present invention and with the Synchron method.

The capillary electrophoresis method of the present invention was also used to determine urine total protein, and the results were compared with those obtained by the Synchron CX4 (Beckman Instruments, Fullerton, Calif.) method. When these results were compared, the correlation coefficient was 0.9867, the slope was 0.83, and the intercept was −0.462 (FIG. 13). This indicated a slightly lower recovery of protein for the capillary electrophoresis method than for the CX4 method.

ADVANTAGES OF THE PRESENT INVENTION

The present invention provides a rapid, efficient, reliable, and reproducible method of determining both the concentration of a marker protein of interest in a sample and the total protein concentration in the sample. The method can be used to detect any protein and has a wide dynamic range. It is relatively resistant to interference because it does not require a specific reaction of a reagent with any particular group of the protein. It is useful for all types of biological samples as well as non-biological samples.

Although the present invention has been described in considerable detail with regard to certain preferred versions thereof, other versions are possible. Therefore, the spirit and scope of the appended claims should not be limited to the descriptions of the preferred versions contained herein.

We claim:

1. A method for quantitating albumin comprising the steps of:
   (a) adding a known quantity of an internal standard compound to a sample containing albumin, the internal standard compound selected from the group consisting of dichlorobenzoic acid and trichlorobenzoic acid and producing a detector signal in relation to its concentration and being capable of electrophoretic separation from albumin;
   (b) subjecting the sample and the internal standard compound to capillary electrophoresis to separate the albumin and internal standard compound from each other and from other components in the sample;
   (c) measuring the detector signal produced by the internal standard compound and a detector signal produced by the albumin to determine a ratio of albumin signal to internal standard signal; and
   (d) determining the concentration of the albumin in the sample from a standard curve of protein concentration versus the ratio of albumin signal to internal standard signal.

2. The method of claim 1 wherein the detector signal is a detectable electromagnetic radiative signal.

3. The method of claim 2 wherein the detector signal is a signal produced by absorption of light in the ultraviolet region of the spectrum, the visible region of the spectrum, or in both the ultraviolet and the visible regions of the spectrum.

4. The method of claim 1 wherein the internal standard compound is selected from the group consisting of a dichlorobenzoic acid and a trichlorobenzoic acid.

5. The method of claim 4 wherein the internal standard compound is a dichlorobenzoic acid.

6. The method of claim 5 wherein the internal standard compound is 2,4-dichlorobenzoic acid.

7. The method of claim 4 wherein the internal standard compound is a trichlorobenzoic acid.

8. The method of claim 7 wherein the internal standard compound is 2,4,6-trichlorobenzoic acid.

9. The method of claim 6 wherein the wavelength at which the absorbance of the separated albumin and internal standard compound is measured is 214 nm.

10. A method for quantitating a protein comprising the steps of:
    (a) adding a known quantity of an internal standard compound to a sample containing at least one protein, the internal standard compound selected from the group consisting of dichlorobenzoic acid and trichlorobenzoic acid producing a detector signal in relation to its concentration, and being capable of electrophoretic separation from the protein;
    (b) subjecting the sample in the internal standard compound to capillary electrophoresis to separate the protein and the internal standard compound from each other and from other components in the sample;
    (c) measuring the detector signal produced by the internal standard compound and a detector signal produced by the protein to determine a ratio of protein signal to internal standard signal;
    (d) determining the concentration of the protein and the sample from a standard curve of protein concentration versus the ratio of protein signal to internal standard signal.

11. The method of claim 10 wherein the protein is selected from the group consisting of albumin, a myeloma protein, prealbumin, retinol-binding protein, $\alpha_1$-antitrypsin, $\alpha_1$-acid glycoprotein, $\alpha_1$-fetoprotein, haptoglobin, $\alpha_2$-macroglobulin, ceruloplasmin, transferrin, $\beta_2$-microglobulin, C-reactive protein, ferritin, and carcinoembryonic antigen.

12. The method of claim 10 wherein the detector signal is a detectable electromagnetic radiative signal.

13. The method of claim 12 wherein the detector signal is a signal produced by absorption of light in the ultraviolet region of the spectrum, the visible region of the spectrum, or in both the ultraviolet and the visible regions of the spectrum.

14.. The method of claim 10 wherein the internal standard compound is selected from the group consisting of a dichlorobenzoic acid and a trichlorobenzoic acid.

15. The method of claim 14 wherein the internal standard compound is a dichlorobenzoic acid.

16. The method of claim 15 wherein the internal standard compound is 2,4-dichlorobenzoic acid.

17. The method of claim 14 wherein the internal standard compound is a trichlorobenzoic acid.

18. The method of claim 17 wherein the internal standard compound is 2,4,6-trichlorobenzoic acid.

19. The method of claim 16 wherein the wavelength at which the absorbance of the separated protein and internal standard compound is measured is 214 nm.

20. A method for determining the total protein concentration in a sample containing at least one protein comprising:

(a) adding a known quantity of an internal standard compound to a sample containing at least one protein, the internal standard compound selected from the group consisting of dichlorobenzoic acid and trichlorobenzoic acid producing a detector signal in relation to its concentration, and being capable of electrophoretic separation from the protein;

(b) subjecting the sample and the internal standard compound to capillary electrophoresis to separate the protein and the internal standard compound from each other and from other components in the sample;

(c) measuring the detector signal produced by the internal standard compound and a total detector signal produced by all proteins in the sample to determine a ratio of total protein signal to internal standard signal; and (d) determining the total concentration of the protein in the sample from a standard curve of protein concentration versus the ratio of total protein signal to internal standard signal.

21. The method of claim 20 wherein the detector signal is a detectable electromagnetic radiative signal.

22. The method of claim 21 wherein the detector signal is a signal produced by absorption of light in the ultraviolet region of the spectrum, the visible region of the spectrum, or in both the ultraviolet and the visible regions of the spectrum.

23. The method of claim 20 wherein the internal standard compound is selected from the group consisting of a dichlorobenzoic acid and a trichlorobenzoic acid.

24. The method of claim 23 wherein the internal standard compound is a dichlorobenzoic acid.

25. The method of claim 24 wherein the internal standard compound is 2,4-dichlorobenzoic acid.

26. The method of claim 23 wherein the internal standard compound is a trichlorobenzoic acid.

27. The method of claim 26 wherein the internal standard compound is 2,4,6-trichlorobenzoic acid.

28. The method of claim 25 wherein the wavelength at which the absorbance of the separated proteins and internal standard compound is measured is 214 nm.

* * * * *